United States Patent [19]
Shilliday

[11] Patent Number: 5,133,659
[45] Date of Patent: Jul. 28, 1992

[54] APPARATUS AND METHOD FOR ADJUSTING A PALATAL EXPANDER

[76] Inventor: Douglas J. Shilliday, 4775 Knightsbridge Blvd., Columbus, Ohio 43214

[21] Appl. No.: 653,166

[22] Filed: Feb. 11, 1991

[51] Int. Cl.$^5$ ............................................. A61C 3/00
[52] U.S. Cl. ........................................ 433/3; 433/7; 433/24
[58] Field of Search .................. 433/3, 2, 4, 5, 7, 18, 433/24, 141, 152, 153, 157, 159, 162; 81/52

[56] References Cited

U.S. PATENT DOCUMENTS

| | | | |
|---|---|---|---|
| 370,204 | 9/1887 | Melotte | 433/162 |
| 2,640,266 | 6/1953 | Sarti | 433/152 |
| 4,483,674 | 11/1984 | Schutz | 433/7 |

FOREIGN PATENT DOCUMENTS

| | | | |
|---|---|---|---|
| 1566245 | 7/1970 | Fed. Rep. of Germany | 433/7 |
| 189125 | 11/1966 | U.S.S.R. | 433/3 |

*Primary Examiner*—Cary E. O'Connor
*Attorney, Agent, or Firm*—Porter, Wright, Morris & Arthur

[57] ABSTRACT

The hand-held adjustment tool includes an elongated handle having an operative end in which an expander-engaging pin is pivotally or rotably mounted. In order to use the adjustment tool, the tool-receiving portion of the palatal expander mounted in the wearer's mouth is sighted, the handle is grasped by the wearer or an assistant, the straight end portion of the pin is inserted in one of the bores of the tool-receiving portion of the palatal expander, the handle is pushed in a direction which causes the pin to pivot on the handle and rotate the tool-receiving portion and associated shaft, thereby exerting a slight laterally outwardly directed force on the palatine bones of the wearer, via the various components of the palatal expander. This pressure is increased by repeating the foregoing steps under the direction of the orthodontist.

6 Claims, 1 Drawing Sheet

APPARATUS AND METHOD FOR ADJUSTING A PALATAL EXPANDER

BACKGROUND OF THE INVENTION

The present invention relates generally to a method and apparatus for adjusting an orthodontic appliance, and more particularly to a hand-held tool and an associated technique employed by the wearer or assistant to adjust the amount of pressure applied by an expansion device to the wearer's teeth and palate.

A palatal expander is a well-known device whose function is to gradually spread the maxillary arch and thereby provide greater space for proper alignment of the upper teeth. Typically, such an appliance is formed with a segmented body disposed in the palatal cavity, a pair of stainless steel wires extending laterally from opposite sides of the body, and a tooth-engaging band secured at the free end of each wire. The bands are secured, for instance, to the first molars and first bicuspids. The segmented body is provided with means for lateral expansion, typically an elongated shaft threadedly mounted in relatively opposing segments of the body. The shaft is formed with an enlargement or turning block having a plurality of radially extending and outwardly opening bores. By rotating the shaft in one direction the body expands laterally, thereby exerting pressure on the banded teeth of the user. This pressure is transferred to the palate and, after a relatively brief period of time, is dissipated by the gradual expansion of the connective tissue or sutures disposed between the palatine bones. Additional pressure must be applied twice a day by turning the shaft to further expand the appliance until the palatine arch has been extended to provide sufficient space for the proper alignment and positioning of the upper teeth. In view of the need for frequent adjustment of the expander, it is desirable for the device to be designed so that the wearer can adjust it. Accordingly, the conventional palatal expander is constructed in such a manner that the wearer can insert a wire or pin into one of the several bores found in the turning portion of the adjustment shaft and pivot the wire, thereby rotating the shaft and expanding the device. This process is repeated until the required pressure is achieved.

In the past, the adjustment tool, known as a wire key, comprised a relatively short, straight segment of wire rigidly extending from a gripping portion. To adjust the palatal expander, the patient would grasp the wire key, insert the hand and key into the mouth, insert the straight end portion of the key into the turning block portion of the stem and pivot the tool, thereby turning the stem and spreading the segments of the expander outwardly.

The old adjustment tool had several drawbacks. The tool was short, so it was difficult to view the instrument in the mirror, as the user's hand would typically block the view. Furthermore, since the entire tool was inserted in the user's mouth, there was a danger of it being swallowed or becoming lodged in the throat. Also, since the tool required the user to insert a finger or fingers into the mouth, there was a likelihood of activating the gag reflex.

The palatal expander of Siatkowski, as disclosed in U.S. Pat. No. 3,977,082, was equipped with an anteriorly or forwardly disposed adjustment stem which was turned by pivoting the wire key adjustment tool to the left or right. In this manner, the problems associated with inserting the wire key far into the mouth were lessened. However, in view of the proximity of the turning block on the Siatkowski expander to the front teeth of the user, it would be difficult to sight and manipulate the wire key into the adjustment stem.

Thus, the present inventor was faced with the problem of devising an adjustment tool and an associated technique that would be easier and safer for the wearer to employ in adjusting the palatal expander.

SUMMARY AND OBJECTS OF THE INVENTION

The present invention comprises a tool and a method for adjusting a palatal expander which is mounted in a wearer's mouth and which includes a rotatable shaft provided with a tool-receiving portion for selective adjustment of the expander. The present tool comprises an elongated handle having an operative end which includes a component or components for pivotally mounting an expander-engaging pin thereon, and an expander-engaging pin provided with a cooperative component or components for pivotally mounting the pin on the handle and with a substantially straight end portion adapted to engage the tool-receiving portion of the palatal expander. The associated method or technique of adjusting the subject palatal expander basically comprises: (a) sighting the tool-receiving portion of the palatal expander; (b) grasping the elongated handle of the hand-operated adjustment tool; (c) inserting an operative end of the handle into the wearer's mouth, said operative end including a component or components for pivotally mounting an expander-engaging pin thereon; (d) inserting a substantially straight end portion of an expander-engaging pin into the tool-receiving portion of the palatal expander, said pin including a cooperative component or components for pivotally mounting said pin on the handle; and (e) pushing the handle in a direction which causes the pin to pivot at the handle and to rotate the shaft of the palatal expander for selective adjustment of said expander.

A primary object of the present adjustment tool and associated technique is to permit the wearer or assistant to adjust it safely, comfortably and easily. A further object of the present invention is to provide an adjustment apparatus which is durable and relatively inexpensive to manufacture. Further objects and advantages of the present invention may be more readily apparent in view of the following drawings and description of the preferred embodiments.

BRIEF DESCRIPTION OF THE DRAWING(S)

DETAILED DESCRIPTION OF THE PREFERRED EMBODIMENTS

Figure 1:
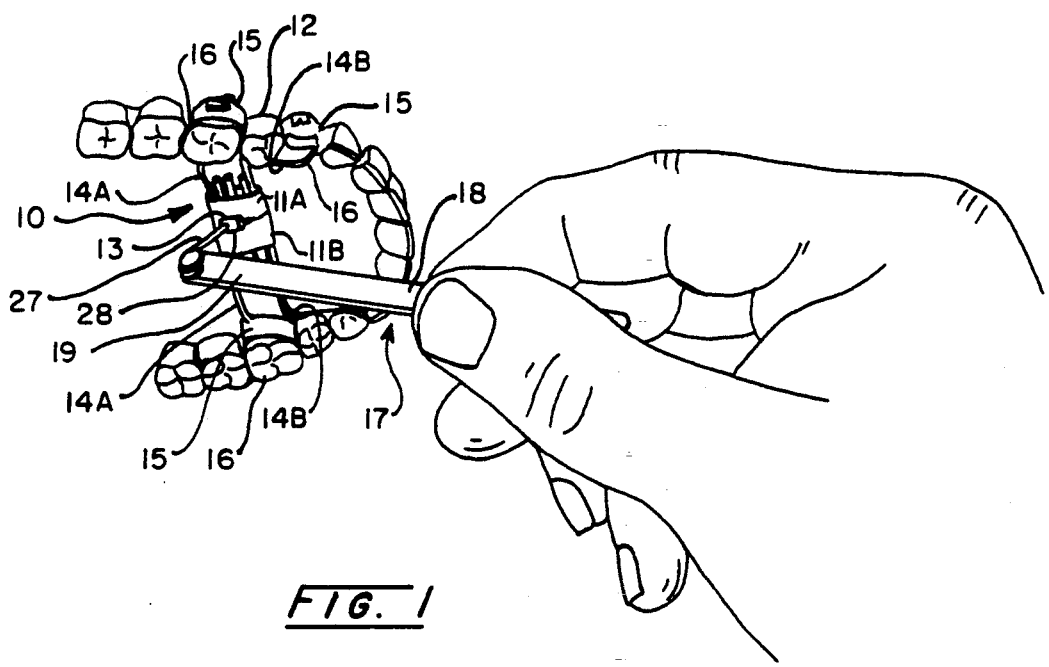
FIG. 1 is a perspective view of one embodiment of the adjustment tool according to the present invention, as well as a typical palatal expander.

Referring now to the drawings, and particularly to FIG. 1, there is illustrated a palatal expander, generally designated 10, of a type well known in the orthodontics art. The expander 10 is typically equipped with a segmented body 11A, 11B, mounted in the palatine cavity near the roof of the wearer's mouth (not shown), a rotatable shaft 12 provided with a tool-receiving portion 13 for selectively adjusting the expander, a pair of stainless steel wires 14A, 14B extending laterally from opposite ends of each body segment 11A, 11B and a separate band 15 for each wire 14A, 14B surrounding one of the upper teeth 16. By adjusting the palatal expander 10, the amount of pressure on the palatine bones and hence, the amount of space between the upper teeth may be controlled in a manner well known in the art and more fully described in the Background of the Invention.

Figure 2:
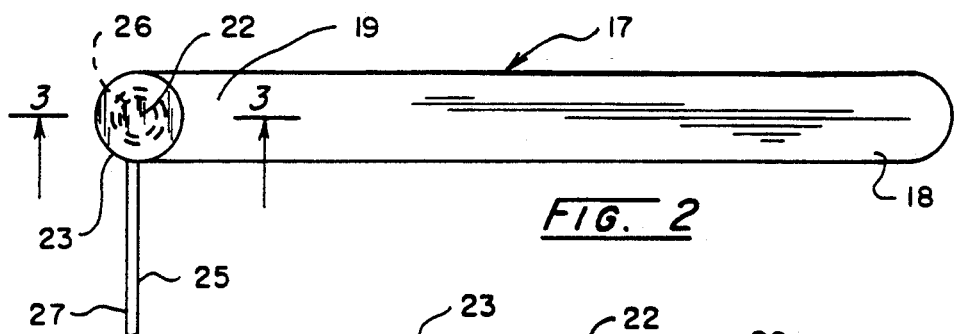
FIG. 2 is an enlarged side view of the adjustment tool shown in FIG. 1.
Figure 3:
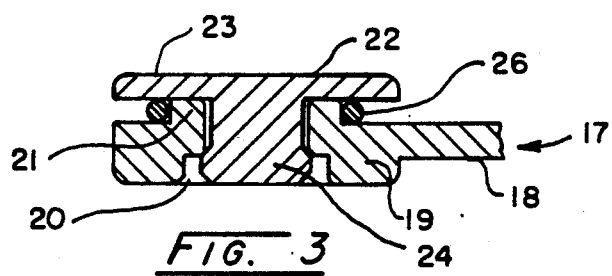
FIG. 3 is a further enlarged selectional view taken along line 3—3 of FIG. 2.

As indicated in FIGS. 2 and 3, one form of the present hand-held adjustment tool, generally designated 17, comprises an elongated handle 18 having an operative end or head 19 formed with a brad-receiving bore 20 extending therethrough and a raised circular shoulder 21 surrounding one of the bore openings. A brad or rivet 22 is formed with an enlarged head 23 and a central plug 24. Preferably, the handle 18 and brad 22 are formed from synthetic resin material and are sized and shaped so that a snap fit is created when the plug 24 is inserted in the bore 20.

An expander-engaging pin or key 25 is formed with a ring-like base portion 26 and with a substantially straight end portion 27. The circular base portion 26 is sized and shaped to be disposed for pivotal or rotational movement relative to the operative end 19 of the handle 18. Preferably, the base 26 is sandwiched between the head 23 of the brad 22 and the handle 18 adjacent to the circular shoulder 21. The straight end portion 27 of the pin or key 25 is sized and shaped to be inserted in each of the several outwardly opening, radially disposed pin-receiving bores 28 (FIG. 1) of the tool-receiving portion 13 of the palatal expander. Preferably, the pin 25 is formed from stainless steel wire of a gauge which prevents it from bending during normal operation.

The present invention also comprehends a unique method or technique of employing the above-described adjustment tool 17. The subject technique or method of adjustment and the adjustment tool 17 are ideally suited for use by the wearer of the palatal expander; however, it is also possible for an assistant to perform the following steps. First, one of the pin-receiving bores 28 of the palatal expander is sighted, either through a mirror by the wearer, or directly by the assistant. The wearer or assistant, whose hand is illustrated in FIG. 1, then grasps the handle 18 of the adjustment tool 17 and inserts the operative end 19 of the adjustment tool 17 into the wearer's mouth. Advantageously, the handle 18 is sufficiently elongated so that, in normal operation, it is unnecessary for any fingers of the wearer or assistant to enter the wearer's mouth. In this manner, the present invention provides a clearer view of the palatal expander, prevents gagging and greatly reduces the danger that the adjustment tool will become lodged in the wearer's mouth or throat. Next, the straight end 27 of the pin 25 is inserted into the bore 28 of the tool-receiving portion 13 of the expander 10. The wearer or assistant then pushes the handle 18 in a direction which causes the pin 25 to pivot at the operative end 19 of the handle 18 and to rotate the tool-receiving portion 13 and shaft 12 of the palatal expander. In the case of the expander illustrated in FIG. 1, the wearer or assistant would push the handle 18 towards the back of the wearer's mouth. In this manner, a relatively small amount of laterally outwardly directed pressure is exerted on the body segments 11A, 11B which, in turn, transfer that pressure to the wearer's palatine bones via the teeth 16, bands 15 and wires 14A, 14B.

The wearer or assistant then retracts the straight end 27 of the pin from the pin-receiving bore 28 of the expander and withdraws the handle 18 sufficiently to permit the pin end 27 to be inserted in another bore 28. The handle 18 is then pushed again towards the back of the mouth, thereby rotating the tool-receiving portion 13 and stem 12 an additional amount and increasing the pressure on the palatine bones. The foregoing steps are repeated a number of times set forth in the orthodontist's instructions. Likewise, the frequency of the entire technique in terms of days and weeks is typically controlled by the orthodontist.

Figure 4:
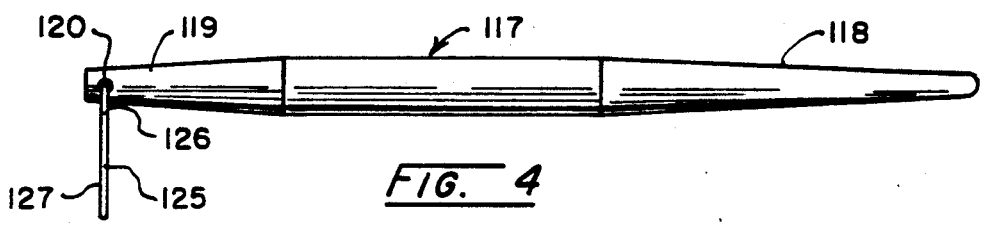
FIG. 4 is a side view of another embodiment of the adjusgment tool according to the present invention.

FIG. 4 illustrates an alternative embodiment of the present invention, wherein the adjustment tool is generally designated 117. The subject tool 117 is equipped with an elongated handle 118, preferably formed from synthetic resin material or stainless steel. The handle 118 is preferably circular in transverse crossection and tapered at opposite ends, whereas the handle 18 illustrated in FIGS. 1–3 is relatively flat and untapered. The handle 118 is provided with an operative end 119 wherein a bore 120 is provided. A pin or wire 125 is pivotally or rotatably mounted on the operative end of the handle 118 and includes a portion 126 cooperative with the handle bore 120 for pivotally or rotatably mounting the pin 125. Preferably, the pin 125 is formed from stainless steel wire and the cooperative portion or stirrup 126 is generally circular or triangular in shape. The pin 125 also includes a substantially straight end portion 127 sized and shaped to engage the tool-receiving bores 28 of the palatal expander 10 in substantially the same manner as the pin 25,27 on the adjustment tool 17. Likewise, the technique set forth above for using the tool 17 is equally applicable to the tool 117.

Other embodiments of the present invention not illustrated in the drawing include an adjustment tool whose handle is equipped or formed with a bulbous end and a pin whose cooperative portion for pivotal connection with the handle comprises a ring or socket that snap fits over the bulbous end of the handle. Thus, while alternative preferred embodiments of the present invention have been illustrated and described in detail, the foregoing description is not intended to limit unduly the gist of the invention or the scope of the following claims.

I claim:

1. A hand-operated tool for adjusting a palatal expander mounted in a wearer's mouth, said palatal expander including a rotatable shaft provided with a tool receiving portion, said tool comprising:

(a) an elongated handle formed from a synthetic resin material, said handle including an operative end provided with a rivet-receiving bore extending therethrough and with a rivet having an enlarged head and a bore-engaging plug portion, said rivet being adapted to be snap-fitted into the rivet-receiving bore in said handle for mounting a pin thereon; and (b) an expander-engaging pin provided with cooperative means for mounting said pin on the handle and with a substantially straight end portion adapted to engage the tool-receiving portion of the palatal expander.

2. A method of adjusting a palatal expander mounted in a wearer's mouth, said palatal expander including a rotatable shaft provided with a tool-receiving portion for selectively adjusting said palatal expander, said method comprising:

(a) sighting the tool-receiving portion of the palatal expander;

(b) grasping an elongated handle of a hand-operated adjustment tool;

(c) inserting an operative end of the handle into the wearer's mouth, said operative end including attachment means for pivotally mounting an expander-engaging pin thereon;

(d) inserting a substantially straight end portion of an expander-engaging pin into the tool-receiving portion of the palatal expander, said expander-engaging pin including cooperative means for pivotally mounting said pin on the handle; and (e) pushing the handle in a direction which causes the pin to pivot at the handle and to rotate the shaft of the palatal expander for selective adjustment of said expander.

3. The method according to claim 2, wherein the handle of the adjustment tool is manipulated by the wearer.

4. The method according to claim 3, wherein the wearer sights the tool-receiving portion of the palatal expander through a mirror.

5. The method according to claim which includes retracting the straight end portion of the expander-engaging pin from the tool-receiving portion of the palatal expander after pushing the handle in a direction which causes the pin to rotate the shaft of said expander; moving the handle in a second direction opposite the direction which causes the pin to rotate the shaft of the palatal expander; reinserting said straight end of said pin into the tool-receiving portion of said palatal expander; and pushing the handle in the direction which causes the pin to rotate the shaft of said palatal expander for selective adjustment thereof.

6. The method according to claim 5, wherein the steps set forth therein are repeated in accordance with an orthodontist's directions.

* * * * *